United States Patent [19]

Pfeiffer et al.

[11] Patent Number: 4,820,517
[45] Date of Patent: Apr. 11, 1989

[54] PROCESS FOR OBTAINING A PEPPER EXTRACT WITH INSECTICIDAL ACTIVITY

[75] Inventors: Hans Pfeiffer, Haan; Manfred Biermann, Muelheim; Peter Schroeder, Viersen; Gerd Goebel, Erkrath; Annemarie Mueller, Monheim, all of Fed. Rep. of Germany

[73] Assignee: Henkel Kommanditgesellschaft auf Aktien, Duesseldorf, Fed. Rep. of Germany

[21] Appl. No.: 878,886

[22] PCT Filed: Jul. 6, 1985

[86] PCT No.: PCT/EP85/00333

§ 371 Date: Jul. 24, 1986

§ 102(e) Date: Jul. 24, 1986

[87] PCT Pub. No.: WO86/01981

PCT Pub. Date: Apr. 10, 1986

[30] Foreign Application Priority Data

Oct. 8, 1984 [DE] Fed. Rep. of Germany ....... 3436859

[51] Int. Cl.$^4$ ............................................. A01K 65/00
[52] U.S. Cl. ........................ 424/195.1; 424/DIG. 10
[58] Field of Search ...................................... 424/195.1

[56] References Cited

U.S. PATENT DOCUMENTS 4,123,559 10/1978 Vitzthum et al. .................... 426/312
4,198,432 4/1980 Vitzthum et al. .................... 426/312
4,490,398 12/1984 Behr et al. ............................ 426/312

OTHER PUBLICATIONS

Agricultural and Food Chemistry 1981, 29,115.

Primary Examiner—John W. Rollins
Attorney, Agent, or Firm—Ernest G. Szoke; Wayne C. Jaeschke; Henry E. Millson, Jr.

[57] ABSTRACT

An insecticidally active fraction is obtained from black pepper by a process comprising the following steps:

(a) extraction of black pepper in ground form with $CO_2$ at 30 to 70° C. and 150 to 500 bar;
(b) removal of sharp tasting fractions therein in a first expansion step at 25 to 35° C. and 70 to 150 bar;
(c) removal of an oily fraction containing the insecticidally active components as well as most of the essential oils in a second expansion step at 15 to 30° C. and 40 to 70 bar;
(d) removal of essential oils by steam distillation, and if desired;
(e) hydrogenation of the insecticidally active components.

16 Claims, No Drawings

PROCESS FOR OBTAINING A PEPPER EXTRACT WITH INSECTICIDAL ACTIVITY

Ordinary commercial insecticides based on synthetic chemicals to be sure are effective, but because of their synthetic origin they are increasingly encountering objections among broad sectors of the population. Therefore, natural plant constituents with insecticidal activity are finding increasing interest. The best known example of this is pyrethrum, from *Chrysanthemum cinerariaefolium*.

Recently it was also found and described that black pepper or an extract of this shows toxic activity against a large number of insects. At first it was suggested that the sharp tasting principle of pepper, piperine or a derivative of piperine, should be considered responsible for the insecticidal activity. In later studies, however, it was shown that it is not piperine but rather other alkaloids of pepper which have insecticidal activity [Su and Horvat, *Agricult. Food Chem.*, Vol. 29, p. 115, 1981]. The authors mentioned extracted ground black pepper with acetone and isolated alkaloids containing amide groups and having insecticidal activity from the extract with the aid of chromatographic methods. Black pepper is the dried, unripe fruit of the tropical plant, *Piper nigrum* L. and contains about 5-10% piperine as well as other sharp tasting alkaloids, 1-2.5% essential oils, and smaller amounts of other alkaloids which are not among the sharp tasting substances.

In addition, spices such as black pepper have already had their flavoring component removed with supercritical gas in terms of temperature and pressure, e.g., $CO_2$, and the extract separated by changing the pressure or temperature (German Preliminary Published Application No. 2,127,611). Spice extracts, e.g., from black pepper, can also be obtained by withdrawing the essential oil acting as a flavor component in a first step with liquid subcritical $CO_2$, and removing the fractions serving as the flavor carrier in a second step with supercritical $CO_2$, separating the extracts by pressure and temperature alterations, and possibly mixing them together (European Patent No. 23,680). In both cases, however, the goal of this process is not directed toward obtaining insecticidally active extracts from black pepper, but rather at the manufacture of scenting or flavoring materials for the food or cosmetic industry.

It has now been found that a non-sharp-tasting fraction bearing insecticidal activity can be extracted from black pepper with compressed $CO_2$ and obtained in pure form under suitable process conditions. In this extraction and recovery process attention is to be paid to the fact that the sharp tasting components, especially the piperine, are not also enriched or separated during the process sequence, since these can lead to mucous membrane irritations during the use of the insecticidal agent in the case of people who intentionally or unavoidably come into contact with the agent. Such an extraction and recovery process must also be economical and able to be carried out in the simplest possible way.

The subject of the invention is a process for obtaining a pepper extract with insecticidal activity, characterized by the following process steps:

(a) extraction of black pepper in ground form with $CO_2$ at 30°–70° C. and 150–500 bar, (b) separation of the sharp tasting fractions in a first expansion step at 25°–35° C. and 70–150 bar, (c) removal of an oily fraction which contains the insecticidally active components as well as most of the essential oils, in a second expansion step at 15°–30° C. and 40–70 bar, (d) obtaining the insecticidally active components by removing the essential oils by steam distillation.

The process can also be carried out by performing the extraction of the black pepper corresponding to the conditions of step (b) with $CO_2$ at 25°–35° C. and 70–150 bar and separating from this by expansion at 15°–30° C. and 40–70 bar according to step (c) an oily fraction, which is further treated according to (d). In this case the sharp tasting components are left behind in the extraction residue and can be obtained from this, possibly by means of a further extraction corresponding to the conditions mentioned under (a).

In a specific embodiment of the process the insecticidally active product of step (d) is hydrogenated in a further step (e). An increase in the insecticidal activity can be achieved in this way. The hydrogenation is carried out according to processes known in and of themselves for the hydrogenation of C—C double bonds, preferably under pressure in the presence of metal catalysts.

Objects of the invention also include the use of processed products as insectidal active ingredients as well as insect control agents containing these active ingredients.

The insecticidal active ingredients obtained in process steps (d) and (e) involve light colored, usually yellow oils, not volatile with steam, which show activity against health pests and nuisance pests such as flies, mosquitoes, roaches, crickets, silverfish, ants, earwigs, wood lice, fleas, lice and bedbugs; wasps, plant pests such as plant lice, cicadas, moth larvae, beetles and their larvae; storage and material pests such as meal beetles, grain weevils, flat grain beetles, golden spider beetles, bread beetles, bean beetles, grain, flour and dry fruit moths; clothing moths, carpet beetles, fur beetles, lard beetles, and dust lice. In particular a marked synergistic activity was found in combination with pyrethrum and synthetic pyrethroids, permitting considerable savings in these relatively expensive materials and/or shorter killing times. The insecticidal active ingredients of the invention are combined with pyrethrum or synthetic pyrethroids in a weight ratio of 1:0.1 to 1:50, preferably 1:0.2 to 1:10.

The oily fraction obtained in process (c) already has insecticidal properties and can be used without further processing as an active ingredient in insect control agents. However, the activity is substantially lower than that of the active ingredients obtained according to (d) or (e). In addition the considerable fraction of essential oils can be undesirable in terms of the specific odor or the risk of contaminations during use.

The essential oils separated by steam distillation according to (d) and the sharp tasting components of the black pepper obtained according to (b) can be used in a known way for producing flavor or aroma concentrates for the food industry, or for odorant compositions for cosmetic purposes and the like.

The active ingredients can be used in the customary formulations, e.g., as solutions, emulsions, suspensions, powders, aerosols, foams, pastes or granulates. The formulations are produced in known ways, e.g., by mixing the active ingredients with extenders such as liquid solvents and/or solid carrier materials. In addition surface-active agents, thus emulsifiers and/or dispersents and/or foam-generating agents, can be used in the formulations. The use of auxiliary solvents, e.g., the use of water as an extender, is likewise possible. In addition, sticking agents, coloring agents, and in the case of aerosols, propellant gases can be added to the formulations. Combinations with other known insecticides and/or synergists, especially pyrethrum or synthetic pyrethroids, as well as mixtures with fungicides, acaricides, repellants, growth regulators and plant nutrients are possible. The content of the insecticidal active ingredient derived from pepper in such formulations amounts to as much as 80%, preferably 0.02 to 50%, by weight.

EXAMPLE 1

Obtaining the Insecticidal Material

The high pressure extraction described below was performed in the unit described in FIG. 1. For this purpose the extraction container E 1 was filled with the ground raw material, the unit purged with $CO_2$, and the extraction conditions established by compressing the $CO_2$ and bringing it to the desired temperature. The removal of the material from the supercritical gas was performed by expansion in two pressure steps in the two separation containers A 1 and A 2. The $CO_2$ was reliquefied, collected in the buffer container B 1 and recompressed to extraction conditions via the membrane piston pump. The operating mode was discontinuous. The extract and the extraction residue were removed from the high pressure containers after the end of the extraction.

Starting Material 20 kg black pepper, origin: Lampong, ground, particle fraction 200 to 400μ.

Step (a): Extraction

Pressure 300 bar, temperature 50° C., time 3 hr, $CO_2$ circulation 10 kg/kg starting material·hr Step (b): Separation First Expansion Step (FIG. 1, A 1)

Pressure 80 bar, temperature 35° C. 1450 g yellow, solid powder (water-free)

Step (c): Separation Second Expansion Stage (FIG. 1, A 2)

Pressure 55 bar, temperature 20° C., 760 g yellow oil (anhydrous)

The extract from the second expansion step (c) was dewatered in a flow centrifuge, and was suitable as an insecticide without further treatment.

Step (d): Steam Distillation

The further purification and obtainment of the insecticidally active components was accomplished by steam distillation as follows:

115 g oil from the second expansion were placed in 500 ml water and subjected to steam distillation for 4 hr. 60.5 g yellow-green pepper oil were removed from the distillate.

The distillation residue was digested with 1 l ether under magnetic agitation, and the ether extract was separated. The ether-soluble insecticidal components (34 g) were obtained as a golden yellow oil by evaporation.

EXAMPLE 2

Obtainment of a Hydrogenated Insecticidal Active Ingredient

An oily product was produced through steps (a)–(d) as in Example 1.

Step (e)

10 g of this oil were dissolved in 25 g methanol, mixed with 1.0 g palladiumcarbon (10.15 wt-% Pd), and hydrogenated for 20 hr at room temperature under a hydrogen pressure of 50 bar. After filtration and removal of the solvent 9.3 g of a pleasant smelling slightly yellow oil remained.

EXAMPLE 3

Testing of Insecticidal Activity

To test the insecticidal activity the substances obtained according to Example 1, process step (c) or (d), in quantities of 1.5 mg, after dilution with acetone, were placed in Petri dishes 10 cm in diameter, and after evaporation of the solvent 10 female flies of the species *Musca domestica* were placed in the covered dishes. The experiment was repeated three times; the following average kill rates were obtained:

|  | Kill rate in % after . . . min: | | | | |
|---|---|---|---|---|---|
|  | 15 | 20 | 30 | 35 | 45 |
| substance from process step (c) | 30 | 47 | 80 | 90 | 100 |
| substance from process step (d) | 40 | 53 | 87 | 100 |  |

To test the synergistic activity, using the same method 1.5 mg of substance according to process step (d) and 0.03 mg pyrethrins, alone and in combination, were tested on resistant flies. The following values were obtained:

|  | Kill rate in % after . . . min: | | | | | |
|---|---|---|---|---|---|---|
|  | 25 | 35 | 40 | 50 | 120 | 150 |
| substance from process step (d) | — | — | — | 50 | 100 | — |
| pyrethrins | — | 50 | — | — | — | 100 |
| pyrethrins + substance from process (d) | 50 | 90 | 100 | — | — | — |

EXAMPLE 4

Testing of Insecticidal Activity

The substances obtained from process steps (d) and (e) of Example 2, in quantities of 0.15 mg, after dilution with acetone were placed in Petri dishes 10 cm in diameter. Following evaporation of the solvent 10 female flies of the species *Musca domestica* were placed in the covered dishes. The following average kill rates were obtained after determination in triplicate:

|  | Kill rate in % after . . . min: | | | | |
|---|---|---|---|---|---|
|  | 25 | 40 | 60 | 90 | 120 |
| substance from process step (d) | — | 3 | 40 | 67 | 73 |
| substance from process step (e) | 10 | 33 | 73 | 93 | 100 |

To determine the synergistic activity, using the same method 0.03 mg pyrethrins alone and in combination with 0.15 mg of the substances from processes (d) and (e) of Example 2 were tested. The following average kill rates were obtained from three experiments in each case:

|  | Kill rate in % after ... min: | | | | |
| --- | --- | --- | --- | --- | --- |
|  | 10 | 20 | 40 | 90 | 150 |
| pyrethrins | — | — | 73 | 80 | 87 |
| pyrethrins + substance from process step (d) | — | — | 90 | 100 | — |
| pyrethrins + substance from process step (e) | 50 | 100 | — | — | — |

We claim:

1. A process for preparing a pepper extract having insecticidal activity comprising the steps of:
    (a) extracting black pepper in ground form with $CO_2$ at a temperature in the range of 30° to 70° C. and a pressure in the range of 150 to 500 bar;
    (b) removing sharp tasting fractions from the resulting extract in a first expansion step at a temperature in the range of 25° to 35° C. and at a pressure in the range of 70 to 150 bar;
    (c) separating an oily fraction containing the insecticidally active components as well as most of the essential oils present in the pepper in a second expansion step at a temperature in the range of 15° to 30° C. and a pressure lower than the pressure in steps (b) in the range of 40 to 70 bar;
    (d) removing the essential oils from the insecticidally active components in the oily fraction by steam distillation.

2. A process according to claim 1 wherein the insecticidally active components obtained in step (d) are hydrogenated.

3. A process according to claim 2 wherein the hydrogenation is carried out under pressure in the presence of a metal hydrogenation catalyst.

4. A process for preparing a pepper extract having insecticidal activity comprising the steps of:
    (a) extracting black pepper in ground form with $CO_2$ at a temperature in the range of 25° to 35° C. and a pressure in the range of 70 to 150 bar;
    (b) isolating an oily fraction from the resulting extract by an expansion step at a temperature in the range of 15° to 30° C. and a pressure in the range of 40 to 70 bar;
    (c) removing essential oils from the oily fraction by steam distillation to produce a residue containing sharp tasting fractions and insecticidally active components; and
    (d) separating the sharp tasting fractions from the insecticidally active components in the residue.

5. The insecticidally active components of black pepper produced by the process of claim 1.

6. The insecticidally active components of black pepper produced by the process of claim 4.

7. A composition for insect control comprising the insecticidally active components of claim 5 and pyrethrum or a synthetic pyrethroid in a weight ratio of from 50:1 to 1:50.

8. A composition for insect control comprising the insecticidally active components of claim 6 and pyrethrum or a synthetic pyrethroid in a weight ratio of from 50:1 to 1:50.

9. A composition according to claim 7 wherein the weight ratio is from 50:1 to 1:10.

10. A composition according to claim 8 wherein the weight ratio is from 50:1 to 1:10.

11. A composition according to claim 7 wherein the weight ratio is 5:1.

12. A composition according to claim 8 wherein the weight ratio is 5:1.

13. A method for controlling insects comprising contacting insects with the insecticidally active substances of claim 5.

14. A method for controlling insects comprising contacting insects with the insecticidally active substances of claim 6.

15. A method for controlling insects comprising contacting insects with the composition of claim 7.

16. A method for controlling insects comprising contacting insects with the composition of claim 8.

* * * * *